USO10632290B2

(12) United States Patent
Young et al.

(10) Patent No.: US 10,632,290 B2
(45) Date of Patent: Apr. 28, 2020

(54) CATHETER ASSEMBLY

(71) Applicant: Tessy Plastics Corporation, Elbridge, NY (US)

(72) Inventors: David R. Young, Syracuse, NY (US); Francis George Tatu, Manlius, NY (US); Willie Werner, Marcellus, NY (US); Vincent Pilletteri, Shortsville, NY (US); Stafford Frearson, Memphis, NY (US); Mark Lattimore, Syracuse, NY (US)

(73) Assignee: Tessy Plastics Corporation, Elbridge, NY (US)

( * ) Notice: Subject to any disclaimer, the term of this patent is extended or adjusted under 35 U.S.C. 154(b) by 280 days.

(21) Appl. No.: 15/662,429

(22) Filed: Jul. 28, 2017

(65) Prior Publication Data
US 2018/0028789 A1 Feb. 1, 2018

Related U.S. Application Data

(60) Provisional application No. 62/367,679, filed on Jul. 28, 2016.

(51) Int. Cl.
*A61M 25/06* (2006.01)
*A61M 25/02* (2006.01)
*A61M 25/00* (2006.01)
*A61M 39/10* (2006.01)

(52) U.S. Cl.
CPC .... *A61M 25/0637* (2013.01); *A61M 25/0009* (2013.01); *A61M 25/0014* (2013.01); *A61M 25/0097* (2013.01); *A61M 25/02* (2013.01); *A61M 39/10* (2013.01)

(58) Field of Classification Search
CPC .......... A61M 25/0637; A61M 25/0009; A61M 25/02; A61M 25/0014
See application file for complete search history.

(56) References Cited

U.S. PATENT DOCUMENTS

| 2,704,074 | A | * | 3/1955 | Butler | A61M 25/0014 604/272 |
| 4,194,504 | A | * | 3/1980 | Harms | A61M 25/0014 604/165.03 |
| 4,366,817 | A | | 1/1983 | Thomas | |
| 4,781,703 | A | * | 11/1988 | Walker | A61M 25/0014 604/264 |
| 4,963,133 | A | * | 10/1990 | Whipple | A61M 25/0014 285/242 |

\* cited by examiner

*Primary Examiner* — Amber R Stiles
(74) *Attorney, Agent, or Firm* — Barclay Damon LLP

(57) ABSTRACT

A catheter assembly comprises a collar assembly comprising a coupling portion proximate the second end and a first compression member configured to removably engage the coupling portion. The catheter assembly further comprises a wing assembly that includes a housing configured to at least partially receive a cannula. The wing assembly also comprises two or more wings extending radially from the housing and a second compression member configured to removably engage a coupling portion. A tube is configured to fluidly couple the collar assembly to the wing assembly, and wherein a portion of the tube is retained by the first and second compression members.

19 Claims, 11 Drawing Sheets

CATHETER ASSEMBLY

CROSS REFERENCE TO RELATED APPLICATION

Pursuant to relevant portions of 35 U.S.C. § 119 and 37 C.F.R. § 1.53, this application claims the benefit and priority of U.S. Patent Application No. 62/367,679, filed on Jul. 28, 2016. The entire contents of this application is hereby incorporated by reference.

TECHNICAL FIELD

This application is directed generally to the field of medical devices and more specifically to a catheter assembly comprising a collar assembly, a wing assembly, and a hollow, flexible tube fluidly connecting the collar assembly to the wing assembly. The application is also directed to a method of manufacturing a catheter assembly without the use of adhesives or other hazardous chemicals or materials.

BACKGROUND

Catheter assemblies are commonplace in the medical field and can be used for a variety of purposes including access to the bladder, blood vessels and epidural space within the spinal column. In most instances, these catheter assemblies are pre-assembled and ready-to-use. This reduces the time it takes to catheterize a patient as well as the human error and potential for infection that would exist if a medical professional were forced to manually assemble the catheter assembly on site.

These catheter assemblies consist of an adapter at one end that can connect the catheter assembly to a dispensing means and a flexible catheter tube with an internal lumen that is fluidly connected to the adapter, collar, or luer at one end and a needle at the other end. The needle end will typically have wings or another type of feature to allow the user to firmly grasp and control the needle during insertion into tissue or other medium. These wings also provide a surface that may be taped or otherwise secured to the patient or another substrate.

Unfortunately, the catheter assemblies currently used in in the medical field suffer from several disadvantages. These catheters tend to use solvent-based adhesives or other forms of chemical bonding to affix the catheter tube to the other components of the assembly. Use of these adhesives can increase the cost of manufacturing and, therefore, the cost of the catheter assembly itself. Moreover, such adhesives or bonding chemicals are hazardous to the environment.

In addition, the catheter assemblies currently used have one or more components that are fabricated from polyvinyl chloride (PVC). This also increases manufacturing cost as special protocols must be adhered to when manufacturing and disposing of PVC. PVC is also very hazardous to the environment. Another disadvantage of the current catheter assemblies is the excessive number of pieces required, which also increases the overall manufacturing cost.

The foregoing background describes some, but not necessarily all, of the problems, disadvantages and shortcomings related catheter assemblies. There is a general and pervasive need in the field to provide a catheter assembly that is environmentally friendly and durable, yet is also inexpensive to manufacture.

SUMMARY

In an embodiment, a catheter assembly comprises a collar assembly having a first end and a second end. The collar assembly further comprises a coupling portion proximate the second end and a first compression member configured to removably engage the coupling portion. The catheter assembly also comprises a wing assembly having a first end and a second end. The wing assembly further comprises an engagement portion proximate the second end, a housing configured to at least partially receive a cannula, two or more wings extending radially from the housing, and a second compression member configured to removably engage the engagement portion. A portion of one end of the tube is retained by the first compression member and a portion of an opposing end of the tube is retained by the second compression member to fluidly couple the collar assembly to the wing assembly.

In another embodiment, the catheter assembly comprises a collar having a first end and a second end and comprising a fluid chamber proximate the first end and a tapered section proximate the second end. The catheter assembly further includes a wing portion comprising a housing configured to at least partially house a cannula, the housing comprising a tapered portion, and a pair of flexible wings configured to couple to a portion of the housing. A tube is further provided having a first end configured to fluidly couple to the tapered section of the collar and a second end configured to fluidly couple to the tapered portion of the wing portion.

An example of an adhesive-free method of assembling a catheter assembly is further provided. The method comprises providing a collar assembly with a coupling portion, that comprises one or more coupling structures. Inserting an end of a flexible tube through a first compression member and over at least a portion of the coupling portion of the collar assembly. Engaging the first compression member with the one or more coupling structures of the coupling portion of the collar assembly to provide a liquid-tight connection between the collar assembly and the flexible tube. Providing a wing assembly comprising a housing configured to retain at least a portion of a cannula. The wing assembly further comprising an engagement portion comprising one or more engagement structures. Inserting an opposite end of the flexible tube through a second compression member and over at least a portion of the engagement portion of the wing assembly. Engaging the second compression member with the one or more engagement structures on the engagement portion of the wing assembly to provide a liquid-tight connection between the wing assembly and the opposite end of the flexible tube.

BRIEF DESCRIPTION OF THE DRAWINGS

So that the manner in which the features of the invention can be understood, a detailed description of the invention may be had by reference to certain embodiments, some of which are illustrated in the accompanying drawings. It is to be noted, however, that the drawings illustrate only certain embodiments of this invention and are therefore not to be considered limiting of its scope, for the scope of the invention encompasses other equally effective embodiments. The drawings are not necessarily to scale, emphasis generally being placed upon illustrating the features of certain embodiments of the invention. In the drawings, like numerals are used to indicate like parts throughout the various views. Thus, for further understanding of the invention, reference can be made to the following detailed description, read in connection with the drawings in which.

DETAILED DESCRIPTION OF THE INVENTION

Figure 1:
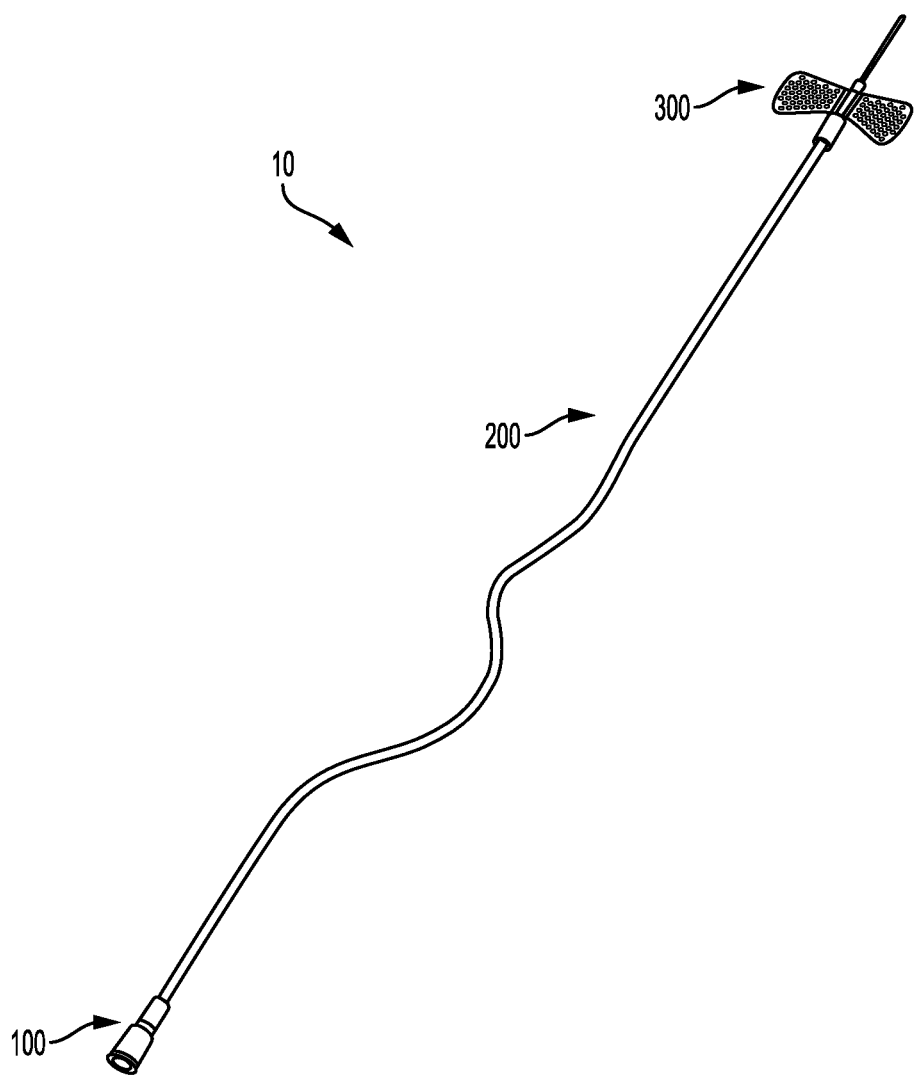
FIG. 1 illustrates an embodiment of the catheter assembly.

Referring to FIG. 1, in one embodiment, the catheter assembly 10 generally comprises a collar or luer assembly 100, a wing assembly 300, and a tube 200 coupling the collar assembly 100 to the wing assembly 300.

Figure 2:
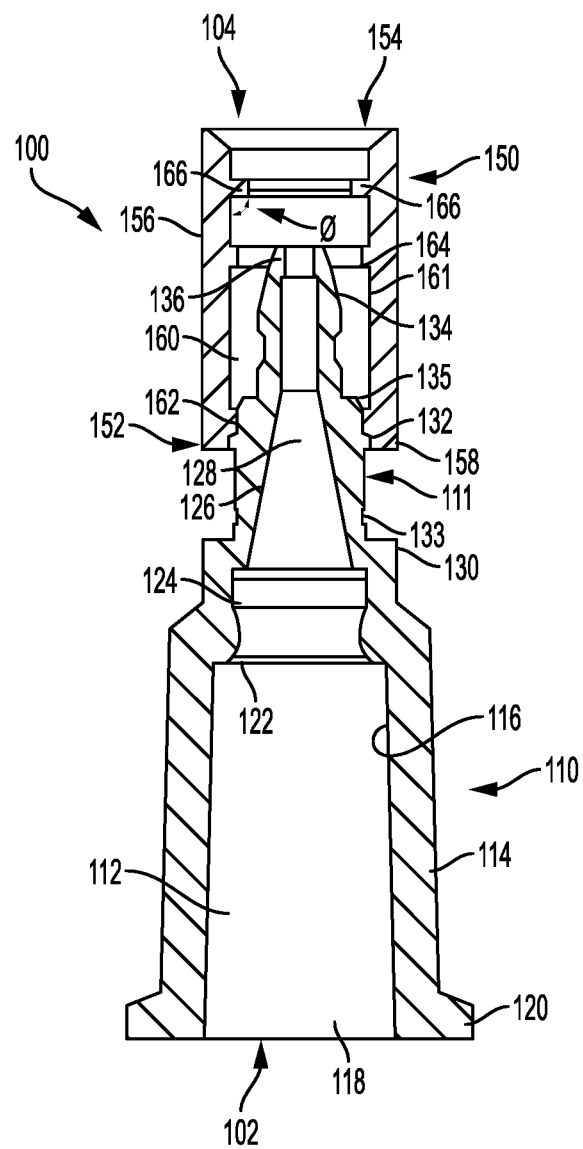
FIG. 2 illustrates a collar assembly of an embodiment of the catheter assembly.

In the embodiment shown in FIG. 2, the collar assembly 100 has a first end 102 and a second end 104. As shown, the collar assembly 100 further comprises a collar 110 or luer with a coupling portion 111 and a compression member 150. The collar 110 has an exterior surface 114, and a fluid chamber 112 defined by an interior surface 116. In other embodiments, the collar 110 does not have a fluid chamber 112. The first end 102 of the collar assembly 100 may be fluidly connected to a source of liquid, such as an intravenous (IV) bag, a collection device, a living organism, or a medical instrument (not shown). As shown, the diameter of the fluid chamber 112 may be greatest at the fluid chamber opening 118 and may decrease towards the tip 136 of the collar 110. Still referring to FIG. 2, the fluid chamber opening 118 may be defined by a flange 120 which may act as a stop member or an anchoring member when the collar 110 is coupled to a fluid source or a medical instrument (not shown).

As shown in FIG. 2, the fluid chamber 112 decreases in diameter along the axis of the collar 110 from the fluid chamber opening 118 to the tip 136 of the collar 110 using one or more stepped portions, one or more converging portions, or a combination of both. In the embodiment of FIG. 2, the decrease in diameter may be accomplished by a stepped portion 124 defined by one or more inner annular shoulders 122 and a converging portion 126 defined by a frusto-conical interior surface 128. As shown, the frusto-conical interior surface 128 may terminate at or near the tip 136 of the collar 110.

Still referring to FIG. 2, the diameter of the exterior surface 114 of the collar 110 may decrease along the axis of the collar 110 from the fluid chamber opening 118 to the tip 136. In an embodiment, this decreasing in diameter may be accomplished through a series of stepped or converging surfaces or a combination of both. A coupling portion 111 of the collar 110 may include a stop member 130, one or more annular notches 132, 133, one or more annular shoulders 135, and at least one bulge or hump feature 134. In another embodiment, the coupling portion 111 of the collar 110 may have one or more annular ridges. The collar 110 may be made of a rigid or semi-rigid, non-reactive material such as polyolefin, thermoplastic polymers such as acrylonitrile butadiene styrene (ABS), or other suitable material.

Still referring to FIG. 2, the compression member 150 has a first end 152, a second end 154, and an exterior surface 156. An interior space 160 is defined by an interior surface 161, which is substantially tubular. As shown, the first end 152 and the second end 154 of the compression member 150 may be open and configured to accept at least a part of the coupling portion 111. In an embodiment, the exterior surface 156 of the compression member 150 may also be substantially tubular. The interior surface 161 may have one or more annular ridges 162, 164 that protrude into the interior space 160. In the pre-assembled state shown in FIG. 2, annular ridge 162 may engage with annular notch 132 of the coupling portion 111 to removeably couple the compression member 150 to the collar 110. In another embodiment, the interior surface 161 may have one or more grooves, ridges, humps, bulges, detents, or any combination thereof. In addition, one or more barbs 166 may be disposed on the interior surface 161 of the compression member 150.

As shown in FIG. 2, the barb 166 may be an annular barb 166 that is formed as part of the compression member 150 and is positioned at an angle Θ that is less than 90° relative to the plane of the interior surface 161 of the compression member 150. In one embodiment, the barb 166 may not be formed as part of the compression member 150. In an embodiment, the barb 166 may be a separate component that can be inserted into the interior space 160 of the compression member 150. In another embodiment, the barb 166 may have a serrated edge. In still another embodiment, more than one barb 166 may be disposed on the interior surface 161 of the compression member 150. The compression member 150 may be made of a semi-rigid or semi-flexible, non-reactive material such as polyolefin, thermoplastic polymers such as acrylonitrile butadiene styrene (ABS), or other suitable material. In some embodiments, the compression member 150 may be at least partially filled with glass.

Figure 3:
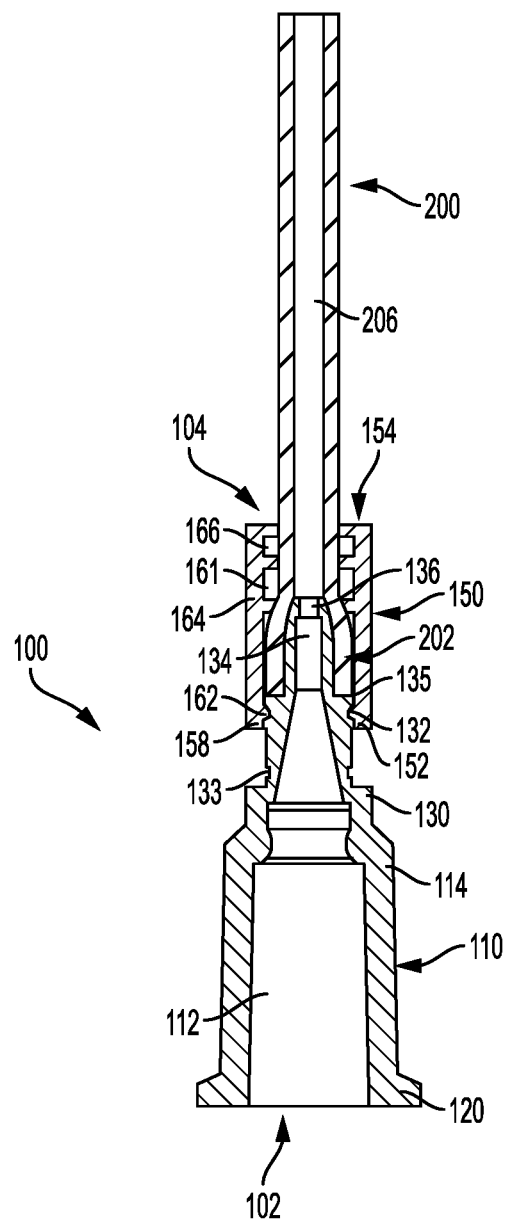
FIG. 3 illustrates the first position of the collar assembly of an embodiment of the catheter assembly.

FIG. 3 depicts the first position of the collar assembly 100. The first position is achieved by inserting one end of the tube 200 into the second end 154 of the compression member 150. The barb 166 may act as a guide for the tube 200 during the insertion process. The angle Θ (FIG. 2) of the barb 166 relative to the plane of the interior surface 161 allows the tube 200 to easily slide past the barb 166 during insertion and acts to bite into or snag the tube 200 when an opposite force is applied to the tube 200, thereby retaining a portion 202 of the tube 200 in the interior space 160. As the tube 200 is inserted into the compression member 150, the tip 136 of the collar 110 is pushed into the lumen 206 of the tube 200 to fluidly connect the tube 200 with the fluid chamber 112. As shown, continued insertion of the tube 200 may cause the bulge 134 of the collar 110 to enter the lumen 206 and create a friction hold to further retain the tube 200 and create a liquid-tight connection. As shown in FIG. 3, the tube 200 may be inserted until it abuts an annular shoulder 135 such that the retained portion 202 of the tube 200 is disposed between the interior surface 161 of the compression member 150 and the exterior surface 114 of the collar 110.

Figure 4:
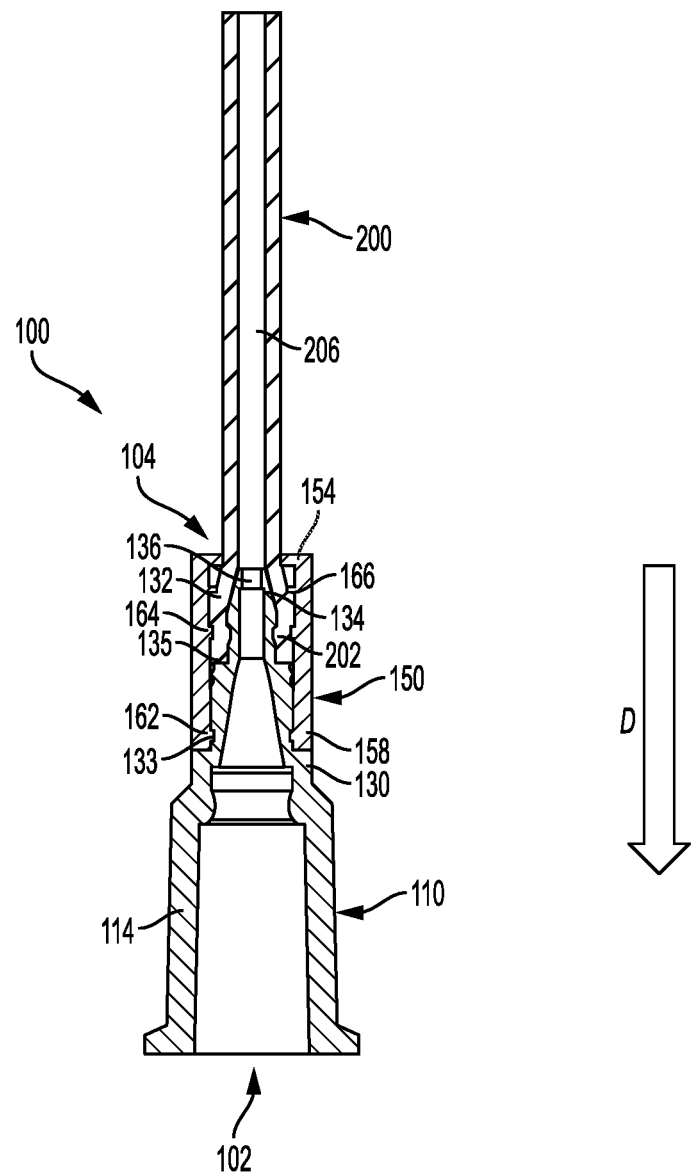
FIG. 4 illustrates the second position of the collar assembly of an embodiment of the catheter assembly.

Once the tube 200 is fully inserted into the collar assembly 100, a force is applied to the compression member 150 in a direction D as shown in FIG. 4. This force may cause the compression member 150 to slide towards the first end 102 of the collar assembly 100 and abut the stop member 130, thereby defining a second position. The force may act to disengage annular ridge 162 of the compression member 150 with annular notch 132 of the coupling portion 111 of the collar 110 and move annular ridge 162 into engagement with notch 133 of the coupling portion 111 of the collar 110 to secure the compression member 150 in the second position. Annular ridge 164 may be brought into engagement with a retained portion 202 of the tube 200 and may act to pinch or compress the retained portion 202 of the tube 200 against the exterior surface 114 of the coupling portion 111 of the collar 110. Still referring to FIG. 4, as the compression member 150 advances toward the stop member 130, the barb 166 may be configured to flex or bend toward the second end 154 of the compression member 150 and compress or pinch part of the retained portion 202 of the tube 200 against the exterior surface 114 of the coupling portion 111 of the collar 110. The compression or pinching of the retained portion 202 of the tube 200 may further act to provide a liquid-tight connection between the lumen 206 of the tube 200 and the fluid chamber 112 of the collar 110. In some embodiments, the barb 166 may have a serrated edge that digs into a portion of the retained portion 202 of the tube 200 to further secure the tube 200 against the exterior surface 114 of the coupling portion 111 of the collar 110. A rearward facing surface 158 of the compression member 150 abuts the stop member 130 thereby preventing over insertion of the compression member onto the collar 110. As shown, the tube 200 may be made of any flexible, non-reactive material such as such as polyolefin, thermoplastic elastomers (TPE), thermoplastic polyurethane (TPU), or other suitable material.

Figure 5:
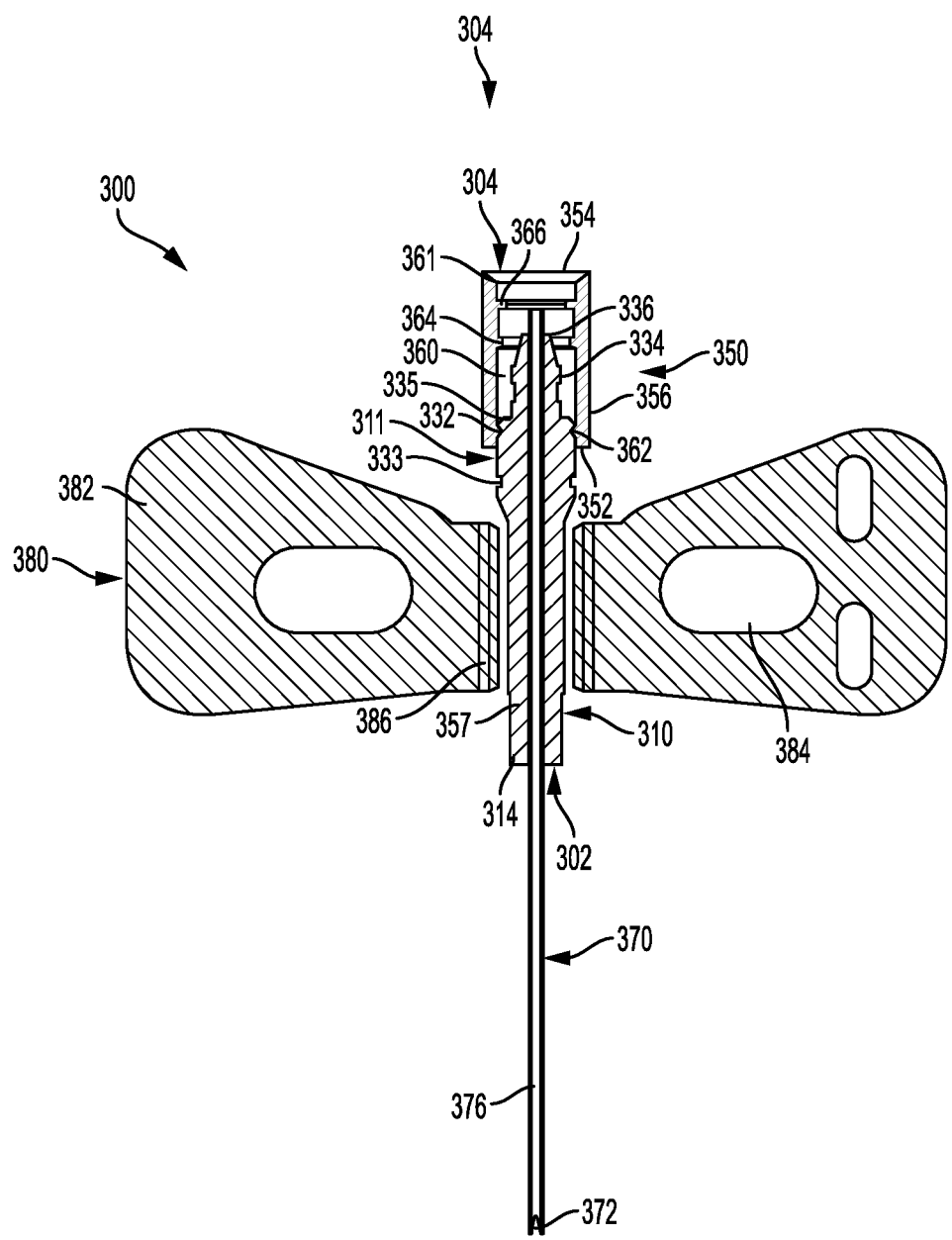
FIG. 5 illustrates an embodiment of a wing assembly of an embodiment of the catheter assembly.

Referring to FIG. 5, the wing assembly 300 has a first end 302 and a second end 304 and comprises a collar or housing 310, a needle or cannula 370, a compression member 350, and a set of wings 380. The housing 310 is over-molded onto a portion of the needle 370 such that, although they are two separate components, they act as one monolithic structure. The diameter of the exterior surface 314 of the housing 310 may vary along its length through a series of stepped surfaces, converging or diverging surfaces, or a combination thereof. The housing 310 may include an engagement portion 311 comprising one or more notches 332, 333, one or more annular shoulders 335, and at least one bulge or hump feature 334. As shown in FIG. 5, the one or more annular shoulders 335 may act as a stop member to prevent over insertion of the tube 200 onto the engagement portion 311. In another embodiment, the housing 310 may have one or more annular ridges, humps, bulges, detents, or any combination thereof. A central bore (not shown) extends the length of the housing 310. The housing 310 may be made of a rigid or semi-rigid, non-reactive material such as polyolefin, thermoplastic elastomers (TPE), thermoplastic polyurethane (TPU), or other suitable material.

The needle or cannula 370 is disposed within the central bore (not shown) of the housing 310. As illustrated in FIG. 5, one end of the needle 370 protrudes from the tip 336 of the housing 310 and the opposing end 372 protrudes from the first end 302. This protrusion of the needle 370 may assist with the over-molding process and may also aid in the fluid connection between the housing 310/needle 370 and the tube 200. The opposing end 372 of the needle 370 is tapered to improve penetration into human tissue or other medium. As shown, the needle is made of stainless steel.

Figure 6:
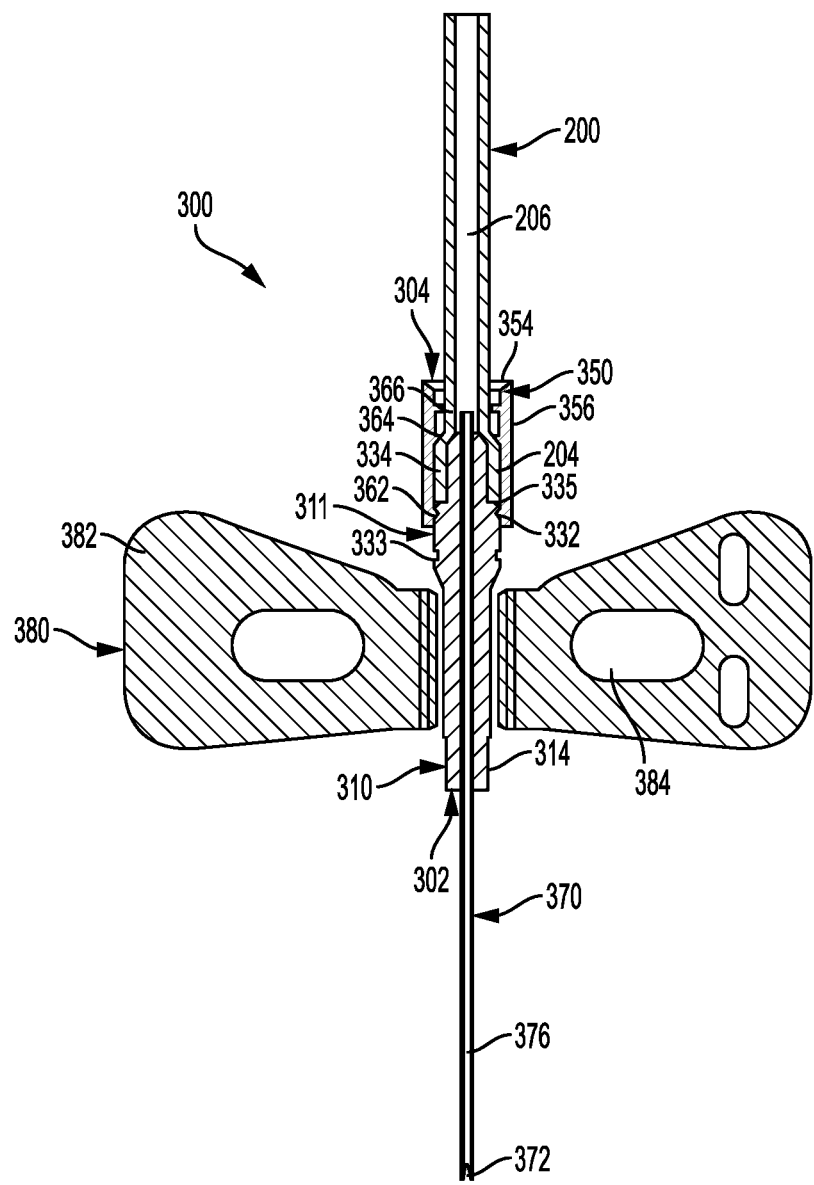
FIG. 6 illustrates the first position of the wing assembly of an embodiment of the catheter assembly.
Figure 7:
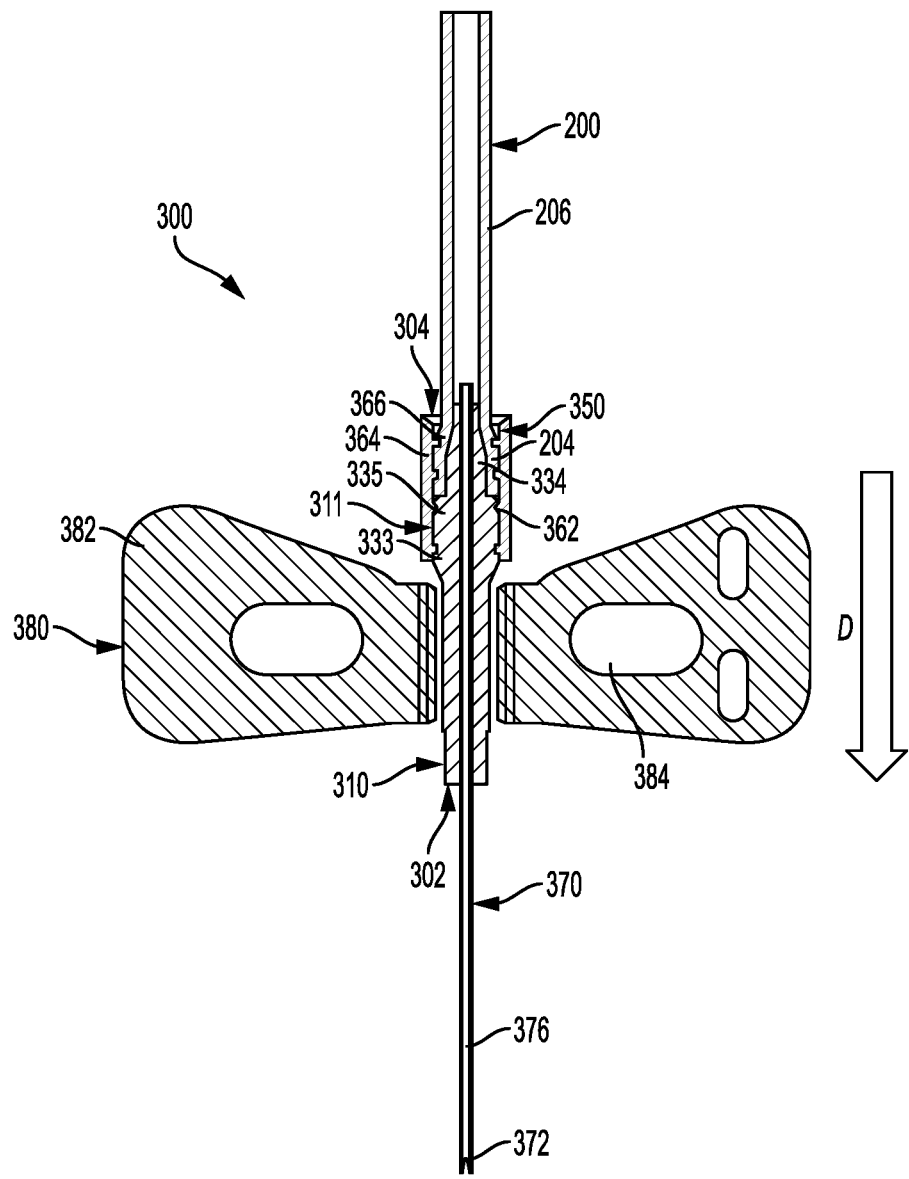
FIG. 7 illustrates the second position of the wing assembly of an embodiment of the catheter assembly.

A set of wings 380 may be attached to the housing 310 at the wing attachment area 357. As shown in FIGS. 5-7, the wings 380 have a top surface 382, a bottom surface (not shown) and an area 386. The top surface 382 and the bottom surface (not shown) define one or more holes 384 configured to improve handling by the user and to reduce the amount of material used during manufacturing. In other embodiments, the top surface 382 and the bottom surface (not shown) of the wings 380 do not define any holes 384. As shown the wings 380 are formed as a single unit with the housing 310, however in other embodiments, the wings 380 may be joined separately to housing 310. The area 386 is disposed between the wings 380 and the housing 310 and is of a reduced thickness as compared to the wings 380 so as to allow a user to flex the wings 380 to better grasp and control the needle 370 for puncture. The wings 380 may be made of the same material as the housing 310, however in another embodiment, the wings 380 and the housing 310 may be made of different materials.

Still referring to FIG. 5, the compression member 350 of the wing assembly 300 may be similar to that of the collar assembly 100 and may work in a similar manner. As shown, the compression member 350 comprises a first end 352, a second end 354, an exterior surface 356 and an interior space 360 defined by an interior surface 361. The first end 352 and the second end 354 of the compression member 350 may be open and configured to accept at least part of the engagement portion 311. In an embodiment, the exterior surface 356 of the compression member 350 may be substantially tubular. The interior surface 361 may have one or more annular ridges 362, 364 that protrude into the interior space 360. In the pre-assembled state shown in FIG. 5, annular ridge 362 may be engaged with notch 332 to removeably couple the compression member 350 to the housing 310. In another embodiment, the interior surface 361 may have one or more annular grooves configured to engage complimentary features on the housing 310. In addition, a barb 366 may be disposed on the interior surface 361 of the compression member 350. As shown, the barb 366 may be formed as part of the compression member 350 and may be disposed at an angle Θ (FIG. 2) relative to the plane of the interior surface 361 of the compression member 350. As shown, the angle Θ (FIG. 2) may be less than 90°. In an embodiment, the barb 366 may not be formed as part of the compression member 350. In another embodiment, more than one barb 366 may be disposed on the interior surface 361 of the compression member 350. The compression member 350 may be made of a semi-rigid or semi-flexible, non-reactive material such as polyolefin, thermoplastic polymers such as acrylonitrile butadiene styrene (ABS), or other suitable material.

FIG. 6 depicts the first position of the wing assembly 300. Said first position is achieved by inserting an opposing end of the tube 200 into the second end 354 of the compression member 350. The barb 366 may act as a guide for the tube 200 during the insertion process. The angle Θ (FIG. 2) of the barb 366 allows the tube 200 to easily slide past the barb 366 during insertion. The barb 366 may bite into or otherwise snag the tube 200 when an opposite force is applied to the tube 200, thereby retaining a portion 204 of the tube 200 in the interior space 160. As the tube 200 is inserted into the compression member 350, the tip 336 of the housing 310 and a portion of the needle 370 may be pushed into the lumen 206 of the tube 200 to fluidly connect the lumen 206 of the tube 200 with the lumen 376 of the needle 370. As shown, continued insertion of the tube 200 may cause the bulge or hump feature 334 of the collar to enter the lumen 206 and deform part of the tube 200 to create a friction hold to further retain the tube 200 and facilitate a liquid-tight seal. As shown in FIG. 6, the tube 200 may be inserted until it abuts the annular shoulder 335 of the housing 310 and the retained portion 202 of the tube 200 is disposed between the interior surface 361 of the compression member 350 and the exterior surface 314 of the engagement portion 311 of the housing 310.

Once the tube 200 is fully inserted into the wing assembly 300, a force is applied to the compression member 350 in a direction D as shown in FIG. 7. This force causes the compression member 350 to move axially towards the first end 302 of the wing assembly 300 and abut the annular shoulder or stop member 335, thereby defining a second position. The force may disengage annular ridge 362 of the compression member 350 with notch 332 of the engagement portion 311 of the housing 310 and move annular ridge 362 of the compression member 350 into engagement with notch 333 of the engagement portion 311 of the housing 310 to secure the compression member 350 in place. Annular ridge 364 of the compression member 350 may be brought into engagement with the tube 200 and may pinch or compress part of the retained portion 204 of the tube 200 against the exterior surface 314 of the engagement portion 311 of the housing 310.

Still referring to FIG. 7, the barb 366 may flex towards the second end 354 of the compression member 350 and may compress or pinch another part of the retained portion 204 of the tube 200 against the exterior surface 314 of the engagement portion 311 of the housing 310. The compression or pinching of the retained portion 204 of the tube 200 further acts to provide a liquid-tight connection between the lumen 206 of the tube 200 and the lumen 376 of the needle 370 and/or the central bore (not shown) of the housing 310. In some embodiments, the barb 366 may have a serrated edge that digs into the retained portion 204 of the tube 200 to further secure the retained portion 204 of the tube 200 against the exterior surface 314 of the engagement portion 311 of the housing 310. As shown, the tube 200 may be made of any flexible, non-reactive material such as polyolefin, thermoplastic elastomers (TPE), thermoplastic polyurethane (TPU), or other suitable material.

Figure 8:
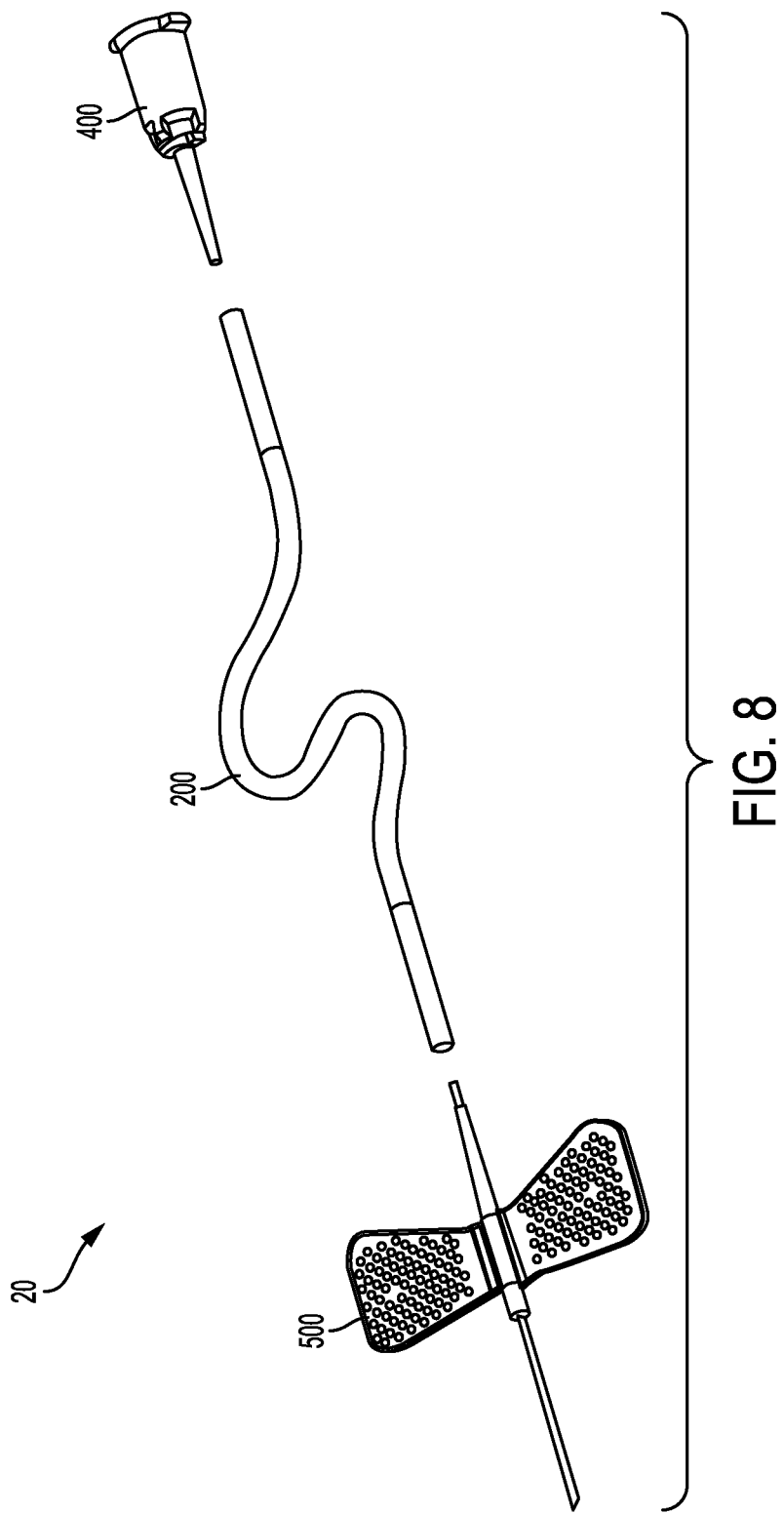
FIG. 8 illustrates an exploded view of an embodiment of the catheter assembly.
Figure 9:
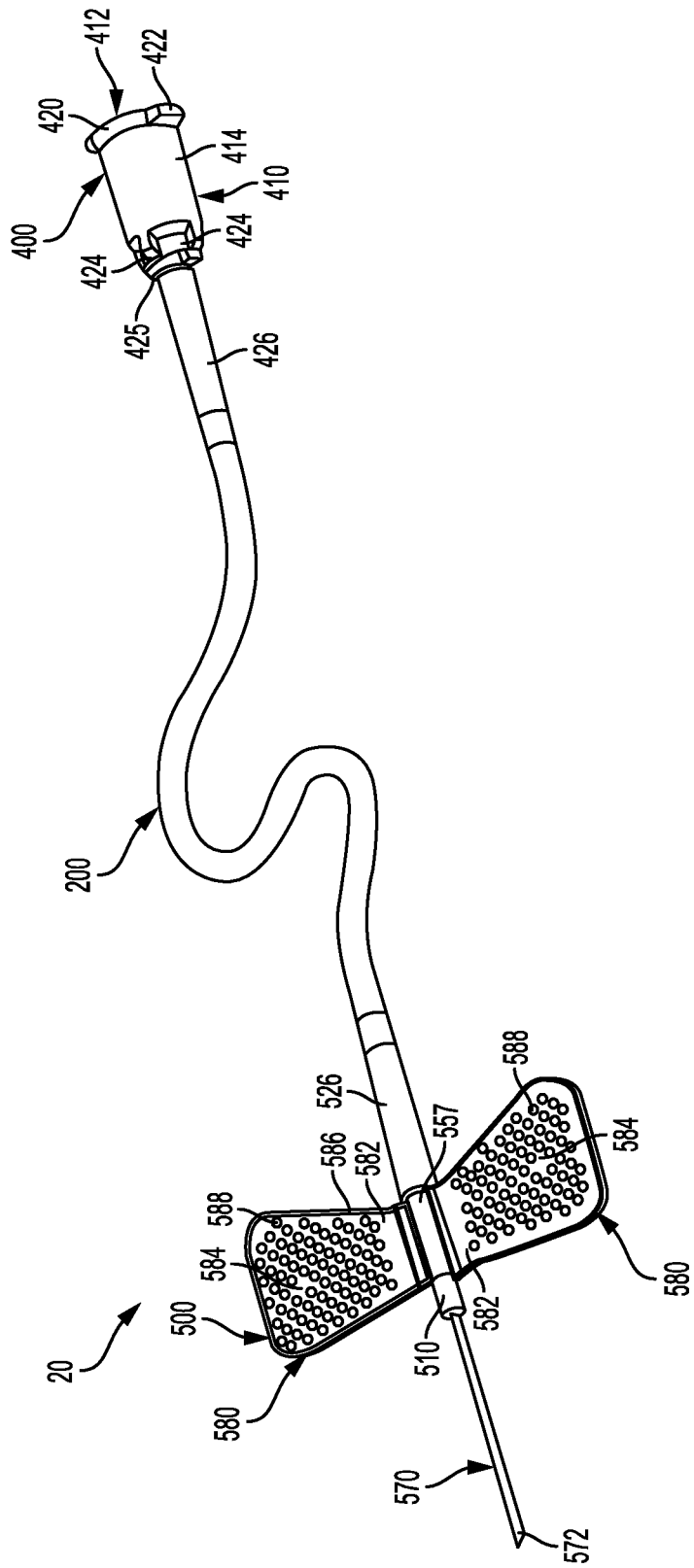
FIG. 9 illustrates an embodiment of the catheter assembly in the assembled position.

As illustrated in FIGS. 8-9, an alternate embodiment of the catheter assembly 20 generally comprises a collar assembly or a luer assembly 400, a wing assembly 500 and tube 200 configured to fluidly connect the collar assembly 400 to the wing assembly 500.

Figure 10:
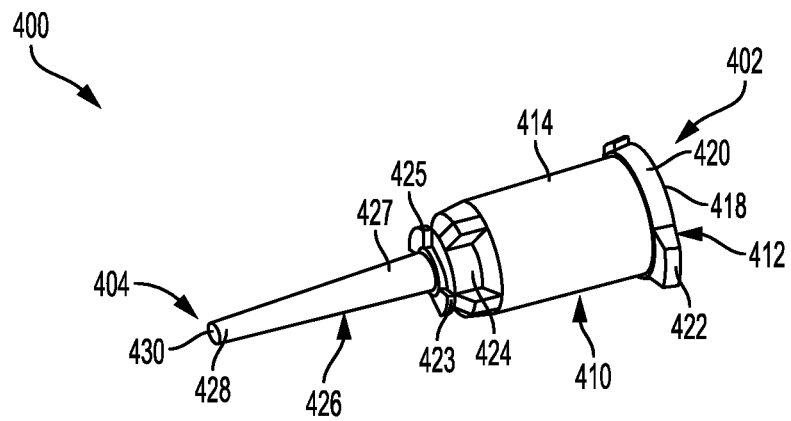
FIG. 10 illustrates a collar assembly of an embodiment of the catheter assembly.

As shown in the embodiment of FIG. 10, the collar assembly 400 comprises a collar 410 having a first end 402 and a second end 404. The first end 402 of the collar 410 may comprise a flange 420 defining an opening 418 to a fluid chamber 412 defined by an interior surface (not shown). The flange 420 may include one or more radial extensions 422, which increase the diameter of the flange 420 and may be used for grasping or anchoring the collar 410. The exterior surface 414 of the collar 410 may be generally tubular in shape with a diameter that is less than the diameter measured at the first end 402.

Referring still to FIG. 10, the exterior surface 414 of the collar 410 may comprise one or more detent surfaces 424, stepped surfaces 423, converging surfaces, or any combination thereof. As shown, the exterior surface 414 of the collar 410 may comprise a frusto-conical surface with a diameter that decreases in diameter along the axis of the collar assembly 400 from the first end 402 to the second end 404. The collar assembly 400 may further comprise a tapered end or a tapered section 426 fluidly connected with the fluid chamber 412. The tapered section 426 includes a first end 427, which opens into the fluid chamber 412 and a second end 428, which defines an orifice 430. As shown in FIG. 10, the tapered section 426 may comprise converging surfaces such that the diameter of the tapered section 426 is smallest at the second end 428. The first end 427 of the tapered section 426 may contact a bottom face 425 of the stepped surface 423.

Figure 11:
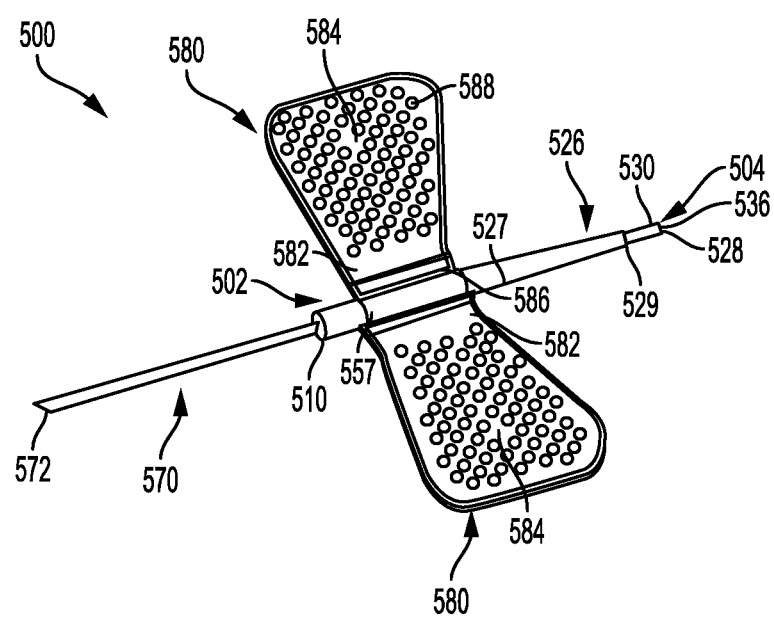
FIG. 11 illustrates a wing assembly of an embodiment of the catheter assembly.

Referring to FIG. 11, the wing assembly 500 or wing portion comprises a first end 502 and a second end 504. A collar or housing 510 is over-molded onto the a portion of a needle 570 such that, although they are two separate components, they act as one monolithic structure. The housing 510 further comprises a tapered end or tapered portion 526 proximate the second end 504. The diameter of the housing 510 may vary along its length through a series of stepped surfaces, converging or diverging surfaces, or a combination thereof. As shown, the housing 510 may further include a tip 536 and a wing attachment portion 557.

The tapered portion 526 has a first end 527 that is proximate the wing attachment portion 557 and a second end 528 that is configured to engage one end of the tube 200. In the embodiment shown in FIG. 11, the diameter of the tapered portion 526 generally decreases from the first end 527 to the second end 528. In an embodiment, the exterior surface of the tapered portion 526 may be frusto-conical and terminate at or near the tip 536. In another embodiment, the tapered portion 526 comprises one or more annular shoulders 529, ridges, grooves, slots, bumps, detents, or other surface features that aid in the assembly and/or use of the wing assembly 500. As shown, the tapered portion 526 may comprise one or more annular shoulders 529. The housing 510 further defines a central bore (not shown) that extends the length of the housing 510 and is configured to at least partially accept the needle 570.

As shown, the housing 510 is formed as a single component, however in other embodiments, the housing 510 may not be formed as a single component. The housing 510 may be made of a rigid or semi-rigid, non-reactive material such as polyolefin, thermoplastic elastomers (TPE), thermoplastic polyurethane (TPU), or other suitable material.

Still referring to FIG. 11, the needle or cannula 570 is disposed within the central bore (not shown) of the housing 510. As shown, the ends of the needle 570 protrude from the housing 510, which may assist with the over-molding process and may also aid in the fluid connection between the housing 510/needle 570 and the tube 200. The opposite end of the needle 572 may be tapered to improve penetration into human tissue or other medium. In another embodiment, only one end of the needle 570 may protrude from the housing 510. As shown, the needle 570 is made of stainless steel, however in other embodiments the needle 570 may not be made of stainless steel.

As illustrated in FIG. 11, in an embodiment, a set of wings 580 may be coupled to the housing 510 at the wing attachment portion 557. Referring to FIGS. 9 and 11, the wings 580 have a top surface 582, a bottom surface (not shown) and an area 586. The top surface 582 and the bottom surface (not shown) may define one or more holes 584 and further include one or more additional gripping elements 588. In other embodiments, the top surface 582 and the bottom surface (not shown) do not define any holes 584 and may not include any additional gripping elements 588. As shown, the wings 580 are formed as a single component with the housing 510, however in other embodiments, the wings 580 may be formed separately from the housing 510. The area 586 is disposed between the wings 580 and the housing 510 and may be of a reduced thickness as compared to the wings 580 to allow a user to flex the wings 580 and better grasp and control the needle 570 for puncture. The wings 580 may be made of the same material as the housing 510, however in anther embodiment, the wings 580 may be made of a different material than the housing 510.

Referring again to FIGS. 9-10, the second end 428 of the tapered section 426 of the collar assembly 400 is inserted into the lumen 206 (FIGS. 3-4, and 6-7) of the tube 200. In an embodiment, the second end 428 is inserted until substantially all of the tapered section 426 is positioned within the lumen 206 (FIGS. 3-4, and 6-7) of the tube 200. As the tube 200 is pulled or pushed onto the tapered section 426 in a direction toward the first end 427, the increasing diameter of the tapered section 426 stretches and deforms the tube 200 to create a liquid-tight friction fit. In an embodiment, the tube 200 is inserted over the tapered section 426 until the end of the tube 200 abuts the bottom face 425 of the stepped surface 423 such that the bottom face 425 acts as a stop to prevent over insertion of the tapered section 426.

As illustrated in FIGS. 9 and 11, the opposing end of the tube 200 is pushed or pulled over the tapered portion 526 of the wing assembly 500. In an embodiment, the tube 200 is positioned such that substantially all of the tapered portion 526 is disposed in the lumen 206 (FIGS. 3-4, and 6-7) of the tube 200. In another embodiment, the tube 200 is pulled over a tube engagement section 530 of the tapered portion 526 until the opposing end of the tube 200 abuts the annular shoulder 529 such the annular shoulder 529 acts as a stop to prevent over insertion of the tapered portion 526. As the tube 200 is pulled or pushed onto the tapered portion 526 toward the first end 527, the increasing diameter stretches and deforms the tube 200 to create a liquid-tight friction fit.

The assembly of the various embodiments of catheter assemblies 10, 20 described herein may be accomplished using a highly controlled automated system at a very fast rate without the use of hazardous chemicals or adhesives.

Additional embodiments include any one of the embodiments described above and described in any and all exhibits and other materials submitted herewith, where one or more of its components, functionalities or structures is interchanged with, replaced by or augmented by one or more of the components, functionalities or structures of a different embodiment described above.

It should be understood that various changes and modifications to the embodiments described herein will be apparent to those skilled in the art. Such changes and modifications can be made without departing from the spirit and scope of the present disclosure and without diminishing its intended advantages. It is therefore intended that such changes and modifications be covered by the appended claims.

Although several embodiments of the disclosure have been disclosed in the foregoing specification, it is understood by those skilled in the art that many modifications and other embodiments of the disclosure will come to mind to which the disclosure pertains, having the benefit of the teaching presented in the foregoing description and associated drawings. It is thus understood that the disclosure is not limited to the specific embodiments disclosed herein above, and that many modifications and other embodiments are intended to be included within the scope of the appended claims. Moreover, although specific terms are employed herein, as well as in the claims which follow, they are used only in a generic and descriptive sense, and not for the purposes of limiting the present disclosure.

The invention claimed is:

1. A catheter assembly comprising:
    a collar assembly having a first end and a second end and comprising
        a coupling portion proximate the second end comprising,
            a first engagement member, and
            a second engagement member,
        a first compression member configured to removably engage the first engagement member to couple the first compression member to the coupling portion in a first position;
        one or more barbs extending from an interior surface of the first compression member;
    a wing assembly having a first end and a second end and comprising,
        a housing configured to at least partially receive a cannula and comprising an engagement portion proximate the second end,
        two or more wings extending radially from the housing, and
        a second compression member configured to removably engage the engagement portion; and
    a tube configured to fluidly couple the collar assembly to the wing assembly, wherein a portion of one end of the tube is retained by the first compression member and a portion of an opposing end of the tube is retained by the second compression member,
    wherein, when the first compression member is in the first position, the one or more barbs allow the portion of the one end of the tube to be advanced in a first direction onto the coupling portion, and wherein the one or more barbs are configured to prevent the portion of the one end of the tube from being pulled in a second direction away from the coupling portion, and
    wherein sliding the first compression member towards the coupling portion disengages the first compression member from the first engagement member and engages the first compression member with the second engagement member to define a second position where axial movement of the tube is prevented in the first direction and the second direction.

2. The catheter assembly of claim 1, wherein the two or more wings are configured to flex.

3. The catheter assembly of claim 1, wherein the collar assembly further comprises a fluid chamber.

4. The catheter assembly of claim 3, further comprising a flange disposed at the first end of the collar assembly, the flange defining an opening to the fluid chamber.

5. The catheter assembly of claim 1 wherein the coupling portion of the collar assembly further comprises a stop member configured to abut an end of the tube.

6. The catheter assembly of claim 1, wherein the second compression member further comprises one or more barbs disposed on an interior surface.

7. The catheter assembly of claim 1, wherein the one or more barbs are disposed at an angle relative to a plane of the interior surface, wherein the angle is less than 90°.

8. The catheter assembly of claim 1, wherein the housing further comprises an area of reduced thickness disposed proximate the wings.

9. The catheter assembly of claim 1, wherein the coupling portion and the engagement portion are configured to be at least partially inserted into opposing ends of the tube.

10. The catheter assembly of claim 9, wherein the first compression member is configured to retain a first portion of the tube between an interior surface of the first compression member and a surface of the coupling portion, and wherein the second compression member is configured to retain a second portion of the tube between an interior surface of the second compression member and a surface of the housing.

11. The catheter assembly of claim 1, wherein the engagement portion of the wing assembly comprises an exterior surface having one or more features configured to engage a portion of the second compression member.

12. The catheter assembly of claim 11, wherein the engagement of the one or more features with the portion of the second compression member restrains axial movement of the second compression member.

13. The catheter assembly of claim 1, wherein the first and second engagement members comprise annular grooves.

14. A catheter assembly comprising:
a collar having a first end and a second end and comprising,
   a fluid chamber proximate the first end, and
   a tapered end proximate the second end, the tapered end comprising a first engagement member and a second engagement member;
a compression member configured to engage the first engagement member to couple the compression member to the second end of the collar in a first position;
a wing portion comprising,
   a housing configured to at least partially house a cannula, the housing comprising a tapered end and a pair of flexible wings configured to couple to a portion of the housing; and
a tube having a first end and a second end, the first end configured to fluidly couple to the tapered end of the collar and be retained by the compression member, and the second end configured to fluidly couple to the tapered end of the wing portion,
wherein sliding the compression member towards the fluid chamber disengages the compression member from the first engagement feature and engages the compression member with the second engagement feature to secure the first end of the tube onto the tapered end of the collar and defining a second position, wherein the first and second engagement members comprise annular grooves.

15. The catheter assembly of claim 14, wherein the compression member further comprises a barb disposed on an inner surface of the compression member and wherein when the compression member is in the first position, the barb is configured to allow the tube to be advanced in a first direction onto the collar and wherein the barb is configured to prevent the tube from being advanced in a second direction away from the collar.

16. The catheter assembly of claim 14, wherein insertion of the first end of the tube onto the tapered end of the collar causes a portion of the first end of the tube to deform to create a liquid-tight seal against the tapered end of the collar.

17. The catheter assembly of claim 16, wherein insertion of the second end of the tube onto the tapered end of the wing portion causes a portion of the second end of the tube to deform to create a liquid-tight seal against the tapered end of the wing portion.

18. The catheter assembly of claim 14, wherein the housing further comprises an area of reduced thickness disposed proximate the pair of flexible wings.

19. An adhesive-free method of assembling a catheter assembly, the method comprising:
providing a collar assembly with a coupling portion, the coupling portion comprising at least a first and a second coupling structure;
inserting an end of a flexible tube through a first compression member and over at least a portion of the coupling portion of the collar assembly;
engaging the first compression member with the first coupling structure of the coupling portion of the collar assembly to define a first position, wherein the end of the flexible tube may be advanced onto the collar assembly but is prevented from being pulled away from the collar assembly when the first compression member is in the first position;
disengaging the first compression member from the first coupling structure;
sliding the first compression member into engagement with the second coupling structure to define a second position wherein a liquid-tight connection between the collar assembly and the end of the flexible tube is achieved and wherein the end of the flexible tube is prevented from being further advanced onto the collar assembly and from being pulled away from the collar assembly;
providing a wing assembly comprising a housing configured to house at least a portion of a cannula, the wing assembly further comprising an engagement portion comprising one or more engagement structures;
inserting an opposite end of the flexible tube through a second compression member and over at least a portion of the engagement portion of the wing assembly; and
engaging the second compression member with the one or more engagement structures on the engagement portion of the wing assembly to provide a liquid-tight connection between the wing assembly and the opposite end of the flexible tube.

* * * * *